United States Patent [19]

Cole et al.

[11] 4,346,168
[45] Aug. 24, 1982

[54] PROCESS FOR THE PREPARATION OF PENICILLIN DERIVATIVES

[75] Inventors: Martin Cole; Robert A. Edmondson, both of Dorking, England

[73] Assignee: Beecham Group Limited, England

[21] Appl. No.: 149,343

[22] Filed: May 13, 1980

[30] Foreign Application Priority Data

May 15, 1979 [GB] United Kingdom ............. 7916921

[51] Int. Cl.³ ............................................. C12P 37/00
[52] U.S. Cl. ................................... 435/43; 260/239.1
[58] Field of Search ........................ 435/43; 260/239.1

[56] References Cited

U.S. PATENT DOCUMENTS 3,528,965 9/1970 Cole et al. ............................. 435/43

FOREIGN PATENT DOCUMENTS 1160211 8/1969 United Kingdom .
1264147 2/1972 United Kingdom .

Primary Examiner—Natalie Trousof
Assistant Examiner—Vera C. Clarke
Attorney, Agent, or Firm—Jacobs & Jacobs

[57] ABSTRACT

A process for the preparation of α-carboxy, 6, α-methoxy penicillin derivatives by the enzymatic hydrolysis of an esterified derivative.

The process is for the preparation of a compound of formula (I):

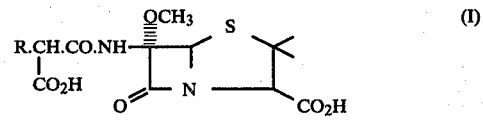

wherein R represents phenyl or 2- or 3-thienyl, which process comprises subjecting a compound of formula (IV):

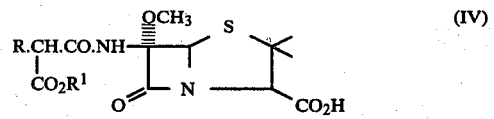

wherein R¹ is an ester-forming radical, to the action of the enzyme α-chymotrypsin or an esterase-producing strain of Streptomyces sp.

6 Claims, No Drawings

PROCESS FOR THE PREPARATION OF PENICILLIN DERIVATIVES

This invention relates to a process for preparation of penicillin derivatives and in particular to the preparation of α-carboxy, 6,α-methoxy penicillin derivatives by the enzymatic hydrolysis of an esterified derivative.

The compounds prepared by the process of this invention have the formula (I):

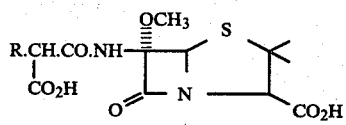

wherein R represents phenyl or 2- or 3-thienyl. Our British Patent No. 1,538,052 discloses compounds of formula (I) wherein R is 2- or 3-thienyl and the compound of formula (I) wherein R represents phenyl is disclosed in British Pat. No. 1,339,007.

One method for the preparation of compounds of formula (I), which is disclosed (for the R=thienyl compounds) in British Pat. No. 1,538,052, comprises reacting a compound of formula (II):

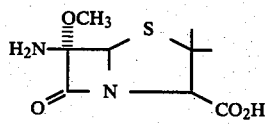

with inter alia an N-acylating derivative of an acid of formula (III):

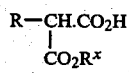

wherein $R^x$ is a carboxyl blocking group, and subsequently removing the group $R^x$. We have now found that ester groups at the α-position can be converted to the free acids by the action of certain enzymes.

The enzymatic hydrolysis of certain α-esters of α-carboxy, 6-H penicillins is disclosed in British Pat. No. 1,160,211. However, the 6-methoxy derivatives of formula (I) above represent a completely different class of compounds and it is not possible to predict whether the enzymes disclosed in Pat. No. 1,160,211 would hydrolyse α-esters of compounds (I) above. In fact some of the enzymes disclosed in Pat. No. 1,160,211 are not useful for preparing compounds of formula (I), one such example being Sepedonium sp.

Accordingly the present invention provides a process for the preparation of a compound of formula (I):

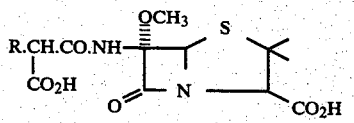

wherein R represents phenyl or 2- or 3-thienyl, which process comprises subjecting a compound of formula (IV):

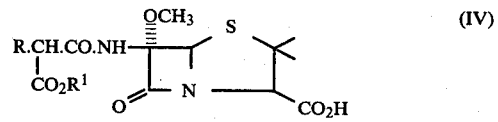

where $R^1$ is an ester-forming radical, to the action of the enzyme α-chymotrypsin or an esterase-producing strain of Streptomyces sp.

Suitable ester-forming radicals $R^1$ include alkyl, aryl or aralkyl groups any of which may be substituted. Examples of such groups include:

(a) $C_{1-6}$ alkyl such as methyl, ethyl, n- and iso-propyl, n-, sec-, iso- and tert-butyl;

(b) substituted $C_{1-6}$ alkyl wherein the substituent is at least one of: chloro, bromo, fluoro, nitro, $C_{1-6}$ alkoxy, $C_{1-6}$ alkoxycarbonyl, cyano, $C_{1-6}$ alkylthio, $C_{1-6}$ alkylamino;

(c) phenyl, benzyl or substituted phenyl or benzyl wherein the substituent is at least one of chloro, bromo, fluoro, $C_{1-6}$ alkyl, $C_{1-6}$ alkoxy, $C_{1-6}$ alkanoyl, $C_{1-6}$ alkoxycarbonyl, nitro or di-($C_{1-6}$)alkylamino.

Preferred ester-forming radicals $R^1$ include $C_{1-6}$ alkyl, phenyl and mono-, di-, and tri-($C_{1-6}$)-alkyl substituted phenyl such as o-, m-, or p-methylphenyl, ethylphenyl, n- or iso-propylphenyl, or n-, sec-, iso- or t-butylphenyl.

Suitable esterase-producing strains of Streptomyces sp. include *S. olivaceus* ATCC 3335 and *S. clavuligerus* ATCC 27064. The esterase enzyme can be prepared by culturing the microorganism or mould in a conventional manner, especially under aerobic conditions in a suitable liquid or semi-solid media. In general, carbon and nitrogen sources which microorganisms can assimilate and inorganic salt nutrients essential for the growth of the microorganisms are included in the culture medium. The culture conditions may be a temperature of from 20° C. to 80° C. and a pH of from 4 to 11. Preferred conditions are 20° C. to 30° C. at a pH of 5 to 9, suitably about pH 7, for 1 to 10 days. The cultured microorganism containing the esterase is employed for the process of this invention in the form of the cultured broth, separated cells, or isolated enzyme.

When α-chymotrypsin is employed as the esterase enzyme for the process of this invention, the enzyme may be employed itself or attached to an insoluble support either by adsorption, for example as disclosed in British Pat. No. 1,264,147, or by covalent bonds either directly or indirectly via bridging groups, for example as described in British Pat. Nos. 1,349,498, 1,387,460 and 1,365,886. Alternatively the enzyme may be bound to a water soluble polymeric support (see Britist Pat. Nos. 1,284,925 and 1,449,808) so that the enzyme/polymer complexes are recoverable from the aqueous reaction mixture by ultrafiltration; or the enzyme may be attached to non-polar groups (and optionally polymeric supports) as described in British Pat. No. 1,463,513, to render the preparation separable from aqueous media by virtue of the affinity for water-immiscible liquids.

The hydrolysis reaction of the present invention is generally carried out in aqueous media, the reaction mixture being maintained in the range pH 5 to 9 and preferably about pH 7. The pH is controlled either by using buffers or by continuous addition of aqueous alkali metal hydroxide until reaction is complete. The temperature of the reaction should be suitable for the enzyme employed and is generally in the range 20° C. to 50° C. preferably 30° C. to 40° C. The reaction time depends on such factors as concentrations of reactants, temperature and pH. After the reaction is complete the reaction mixture is acidified and the penicillin derivative of formula (I) isolated by conventional methods. It is usually convenient to precipitate the compound (I) as an alkali metal salt, for example the disodium salt.

This invention is illustrated by the following assays and Examples.

Assay Method

The compound of formula (I) wherein R is 3-thienyl will be referred to herein as comound AB17421. In order to illustrate the rate of hydrolysis of esters of compound AB17421 by a number of enzymes according to this invention, esters were subjected, in aqueous reaction mixtures, to the action of the particular enzyme and the percentage of hydrolysis of the ester was determined after time intervals using the following assay method:

5 μl samples are removed from the reaction mixtures and spotted on to Whatman No. 1 chromatograpy tapes 1 cm wide. 5 μl samples of standard solutions of AB 17421 are spotted on to separate tapes. The tapes are developed by descending chromatography using butanol/ethanol/water (4:1:5 top phase) for 16 hours and dried thoroughly. [AB17421 runs very close to the origin (Rf=0.035) whilst the esters generally run much nearer the solvent front in this solvent.] A section of tape 10 cm long, including 2 cm behind the origin, is cut off and placed in contact with Blood Base Agar (Oxoid) CM55 seeded with *Escherichia coli* ESS, a sensitive mutant. The plates are incubated at 37° C. for about 5 hours then overnight at 28° C. The diameters of the zones of inhibition are measured and the percentage conversion to AB17421 is calculated with reference to the standard line of diameter of antibiotic zone against the log of the concentration.

Assay 1

De-esterification of α-esters of AB17421 by esterase from Streptomyces sp.

(a) cultivation step

Two strains of Streptomyces sp. (*S. olivaceus* ATCC 3335 and *S. clavuligerus* ATCC 27064) were grown in 500 ml shake flasks containing 100 ml medium at 26° C. for 5 days with shaking. The medium consisted of:

| Glycerol | 1% | |
|---|---|---|
| Arkasoy* | 1.5% | pH 7.0 |
| potassium dihydrogen phosphate | 0.1% | |

[*Arkasoy is soya bean flour supplied by British Arkady Company, Old Trafford, Manchester, U.K.]

(b) hydrolysis reaction

The culture prepared in step (a) was used directly, without separation of the bacteria from the nutrient solution, for the hydrolysis of the α-(p-methylphenyl) ester and the α-ethyl ester of compound AB17421. The reaction mixture consisted of 0.5 ml of a solution of 8 mg/ml of the ester in 0.05 M potassium phosphate buffer plus 0.5 ml of fully grown culture. The formation of AB17421 was determined as in the assay method above. The percentages of hydrolysis after 3 and 6 hours are given in Table 1 below.

TABLE 1

| | p methyl phenyl ester | | ethyl ester | |
|---|---|---|---|---|
| Reaction Time | *S. olivaceus* | *S. clavuligerus* | *S. olivaceus* | *S. clavuligerus* |
| 0 | 7% | 7% | 0 | 5% |
| 3 hours | 75% | 66% | 7% | 27% |
| 6 hours | 87% | 79% | 15% | 48% |

Assay 2

De-esterification of α-esters of AB17421 by esterase from *Streptomyces clavuligerus* grown in various media (a) cultivation methods A slope culture of a re-isolate of *Streptomyces clavuligerus* ATCC 27064 grown on agar of the composition given below was transferred to 100 ml of a seed stage medium (Medium 1 below) in a 500 ml plugged (porous plastic foam) conical flask. The seed stage flask was shaken at 26° C. for 2 days and then 5 ml portions were added to 500 ml conical flasks containing 100 ml of the media listed below. After inoculation the flasks were shaken at 26° C. for a further 4 days, after which the cells were centrifuged off at 12,000 r.p.m. for 20 minutes. The supernatant was poured off and used as source of enzyme.

Composition of Agar-Slope Medium
Dextrin - 10.0 g
K$_2$HPO$_4$ - 1.0 g
MgSO$_4$.7H$_2$O - 1.0 g
NaCl - 1.0 g
(NH$_4$)$_2$SO$_4$ - 2.0 g
CaCO$_3$ - 2.0 g Trace Salts Solution
FeSO$_4$.7H$_2$O - 0.1 g
MnCl$_2$.4H$_2$O - 0.1 g
ZnSO$_4$.7H$_2$O - 0.1 g
Distilled water - 100 ml Trace salts solution - 1 ml
Difco agar - 20.0 g
Distilled water - 1000 ml
pH 7.0 to 7.4

Medium 1 (also used as the seed stage medium)
Glycerol - 1%
Arkasoy - 1.5%
KH$_2$PO$_4$ - 0.1% pH adjusted to 7.0 with NaOH

Medium 2
Soluble starch - 2%
Glycerol - 0.3%
Scotasol - 0.1%
Arkasoy - 1%
FeSO$_4$.7H$_2$O - 0.01%
in deionized water Medium 3
Dextrose - 1%
Soyabean Meal - 1%
Scotasol - 0.05%
CaCO$_3$ - 1%
in deionized water Medium 4
Glycerol - 2%
Soyabean Meal - 1.5%
MgSO$_4$ - 0.1%
K$_2$HPO$_4$ - 0.1%
in deionized water Medium 5
Glucose - 2%
Lab Lemco (Oxoid) - 1%
Oxoid Yeast Extract - 0.3%
CaCO$_3$ - 0.3%
in deionized water (b) hydrolysis reactions The reaction mixtures contained 0.5 ml of the α-(o-methyl-phenyl) ester of AB17421 at 8 mg/ml in 0.05 potassium phosphate buffer pH 7.0 together with 0.5 ml of the culture supernatant of *Streptomyces clavuligerus* grown in the media described above. The control reaction contained buffer instead of culture supernatant. The reaction mixtures were incubated for 6 hours at 37° C. with occasional shaking. The percentage of AB17421 formed after 3 and 6 hours, determined by the assay method above, are shown in Table 2. The figures in Table 2 are means of duplicates.

TABLE 2

| Reaction Time | % conversion to AB17421 | | | | | |
|---|---|---|---|---|---|---|
| | Control | Medium | | | | |
| | | 1 | 2 | 3 | 4 | 5 |
| 0 | 0 | 0 | 0 | 0 | 0 | 0 |
| 3 hours | — | 10% | 6% | 17% | 10% | 41% |
| 6 hours | 13% | 20% | 7% | 31% | 13% | 66% |

Assay 3

De-esterification of α-esters of AB17421 by chymotrypsin

Chymotrypsin (supplied by Koch Light Limited and crystallised 3 times) was dissolved in 0.05 M pH 7 potassium phosphate buffer at 4 mg/ml and mixed in 1:1 v/v ratio with 8 mg/ml solutions of the following α-esters of AB17421 dissolved in pH 7 0.05 M potassium phosphate buffer: phenyl, o-methylphenyl, o-ethylphenyl, p-methylphenyl, ethyl and isobutyl. The reaction conditions were as in assay 1 and control reactions were set up with 0.05 M potassium phosphate buffer in place of the enzyme. The percentage of AB17421 formed after 3 and 6 hours, determined by the assay method above, are shown in Table 3.

TABLE 3

| Reaction Time | phenyl | | o-methyl-phenyl | | o-ethyl-phenyl | |
|---|---|---|---|---|---|---|
| | Experimental | Control | Experimental | Control | Experimental | Control |
| 0 | 24% | 2% | 3% | 0 | 3% | 0 |
| 3 hours | 80% | 10% | 60% | 2% | 36% | 2% |
| 6 hours | 80% | 19% | 69% | 4% | 44% | 4% |

| Reaction Time | p-methyl-phenyl | | ethyl | | isobutyl | |
|---|---|---|---|---|---|---|
| | Experimental | Control | Experimental | Control | Experimental | Control |
| 0 | 6% | 0 | 0 | 0 | 2% | 0 |
| 3 hours | 85% | 11% | 53% | 0 | 14% | 0 |
| 6 hours | * | 18% | * | 0 | 22% | 0 |

*not sampled

Assay 4

De-esterification of the α(o-methyl-phenyl) ester of AB17421 by chymotrypsin bound to a solid support A reaction was set up containing the o-methylphenyl α-ester of AB17421 at 4 mg/ml of Enzite-CHT (chymotrypsin bound to carboxymethyl cellulose) (supplied by Miles Seravac Limited, Moneygrow Green, Holyport, Maidenhead, Berkshire) at 10 mg/ml, in 0.05 M potassium phosphate buffer pH 7.0. The reaction was incubated at 37° C. with continuous stirring and 5 µl samples were taken for assay as described above. A control reaction was set up with 0.05 M potassium phosphate buffer in place of the enzyme. The results are shown in Table 4.

TABLE 4

| Reaction Time | % conversion to AB17421 (bound enzyme) | % conversion to AB17421 (control reaction) |
|---|---|---|
| 0 | 0 | 0 |
| 3 hours | 26% | — |
| 6 hours | 45% | 15% |

EXAMPLE 1

Preparation of disodium 6,β[2-carboxy-(3-thienyl)acetamido]-6,α-methoxy penicillanate (AB17421) by enzymic de-esterification of the 2-(p-methylphenyl) ester Water (8 ml) containing 0.5 g of the 2-(p-cresyl)ester of AB17421, adjusted to pH 7.0, was mixed with 2 ml water containing 50 ml chymotrypsin (Koch Light), and adjusted to pH 7.0. The mixture was incubated at 37° C. and the pH was continuously controlled at 7.0 by the addition of 0.25 N NaOH from an automatic titrator. After 24 hours no ester remained as shown by thin layer chromatography using chloroform/acetone/acetic acid 7:7:1 on silica gel and spraying with 2% phosphomolybdic acid in ethanol.

The pH of the reaction mixture was adjusted to 4.0 with N HCl and was shaken with 2×10 ml diethyl ether to remove the p-cresol. The solvent layer was discarded and the pH of the aqueous layer was adjusted to pH 2.0. Ethyl acetate (10 ml) was added to extract the AB17421 and the layers were mixed thoroughly. The organic phase was collected, washed with water and salt solution to remove precipitated protein and evaporated to dryness.

The dried material was dissolved in acetone and 0.72 ml of 2 N sodium ethyl hexoate in methyl isobutyl ketone was added to precipitate the AB17421 as a disodium salt, which was filtered off and dried thoroughly to give 0.3 g white powder.

This material was analysed by high performance liquid chromatography using a µ Bondapak $C_{18}$ column (Waters Associates) at 2 ml/min with the following solvent: 95% 0.05 M sodium acetate pH 6.5, (adjusted with acetic acid) and 5% methanol.

Two peaks were seen, the retention times being 4.7 minutes and 3.9 minutes which is identical with that seen for the isomers at the 2-position in the side-chain for a standard sample of AB17421 (disodium salt) prepared by synthetic chemical means. By measurement of peak heights the purity was calculated to be 80.4%.

The n.m.r. analysis of the material was the same as that seen for a preparation of AB17421 made by chemical means.

Paper chromatographic analysis of the material was carried out on a 4 mg/ml solution in water alongside a similar solution of AB17421 made by chemical means. Samples (5 µl) were spotted onto paper tapes which were developed overnight using three different solvents. The positions of the zones were located by contacting the paper tapes with nutrient agar seeded with *Escherichia coli* ESS, and incubation overnight at 28° C.

The zone diameters and Rf values are listed below:

| Solvent | AB17421 (synthetic chemical preparation) | | AB17421 (made in Example 1) | |
|---|---|---|---|---|
| | zone diameter | Rf | zone diameter | Rf |
| n-Butanol/ethanol/water 4:1:5 v/v (top phase) | 34.7 | 0.08 | 34.7 | 0.08 |
| n-Butanol/acetic acid/water 12:3:5 v/v | 32.6 | 0.90 | 32.6 | 0.90 |
| n-Butanol/pyridine/water 1:1:1 v/v | 32.8 | 0.55 | 32.2 | 0.55 |

It was concluded that the material prepared by the enzymic process in the example was an authentic preparation of the sodium salt of 6-β-[2-carboxy-(3-thienyl)acetamido]-6-α-methoxy penicillin (AB17241).

We claim:

1. A process for the preparation of a 6α-methoxy penicillin of formula (I):

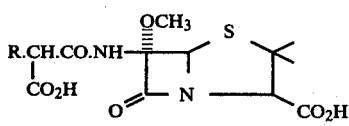

wherein R represents phenyl or 2- or 3-thienyl, which process comprises subjecting a compound of formula (IV):

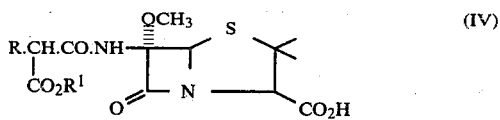

where $R^1$ is an ester-forming radical, to the action of the enzyme α-chymotrypsin or an esterase-producing strain of Streptomyces sp.

2. A process as claimed in claim 1 wherein $R^1$ is an optionally substituted alkyl, aryl or aralkyl group.

3. A process as claimed in claim 1 wherein $R^1$ is $C_{1-6}$ alkyl, phenyl or mono-, di-, or tri-$(C_{1-6})$-alkyl substituted phenyl.

4. A process as claimed in claim 1 wherein R represents 3-thienyl.

5. A process as claimed in claim 1, wherein the esterase-producing strain of Streptomyces sp. is *Streptomyces olivaceus* ATCC 3335 or *Streptomyces clavuligerus* ATCC 27064.

6. A process as claimed in claim 1, wherein the esterase-producing strain is *Streptomyces olivaceus* ATCC 3335.